(12) United States Patent
Faubert et al.

(10) Patent No.: US 8,369,955 B2
(45) Date of Patent: Feb. 5, 2013

(54) METHOD AND SYSTEM FOR IMPROVING A SUBJECT'S SENSORY, REFLEX AND/OR MOTOR MECHANISMS VIA AUDITORY, TACTILE OR VISUAL STIMULATIONS

(75) Inventors: Jocelyn Faubert, Montreal (CA); Rafael Doti, Montreal (CA); Jesus-Eduardo Lugo-Arce, Laval (CA)

(73) Assignee: Valorisation-Recherche, Limited Partnership, Montreal, Quebec (CA)

( * ) Notice: Subject to any disclaimer, the term of this patent is extended or adjusted under 35 U.S.C. 154(b) by 740 days.

(21) Appl. No.: 12/446,338

(22) PCT Filed: Oct. 22, 2007

(86) PCT No.: PCT/CA2007/001872
§ 371 (c)(1),
(2), (4) Date: Oct. 2, 2009

(87) PCT Pub. No.: WO2008/046231
PCT Pub. Date: Apr. 24, 2008

(65) Prior Publication Data
US 2011/0005532 A1    Jan. 13, 2011

Related U.S. Application Data

(60) Provisional application No. 60/852,972, filed on Oct. 20, 2006.

(51) Int. Cl.
*A61N 1/02* (2006.01)

(52) U.S. Cl. .............. 607/48; 607/1; 600/555; 600/558; 600/559; 600/28

(58) Field of Classification Search .................. None
See application file for complete search history.

(56) References Cited

U.S. PATENT DOCUMENTS

| 4,966,164 | A | 10/1990 | Colsen et al. |
| 6,001,072 | A | 12/1999 | Fujiwara |
| 6,285,905 | B1 | 9/2001 | Chang et al. |
| 2002/0010497 | A1* | 1/2002 | Merfeld et al. ................ 607/62 |
| 2004/0073271 | A1 | 4/2004 | Harry et al. |
| 2004/0173220 | A1 | 9/2004 | Harry et al. |
| 2006/0017548 | A1 | 1/2006 | Ozaki et al. |
| 2006/0020452 | A1 | 1/2006 | Nakatani et al. |
| 2006/0167524 | A1 | 7/2006 | Kimura et al. |

FOREIGN PATENT DOCUMENTS

| JP | 2002-182674 | 6/2002 |
| JP | 2003/048453 | 2/2003 |
| JP | 2005-137618 | 6/2005 |
| JP | 2005-211165 | 8/2005 |

(Continued)

OTHER PUBLICATIONS

Cohen et al., "Functional Relavance of Cross-modal Plasticity in Blind Humans", Sep. 1997, Nature, vol. 389, p. 180-183.*

(Continued)

*Primary Examiner* — Kennedy Schaetzle
(74) *Attorney, Agent, or Firm* — Fay Kaplun & Marcin, LLP

(57) ABSTRACT

The present invention relates to a method and a system for improving sensitivity of a first sensory, reflex and/or motor mechanism of a subject by stimulating a second sensory, reflex and/or motor mechanism of the subject. For that purpose a noise is applied to the second sensory, reflex and/or motor mechanism to improve the sensitivity of the first sensory, reflex and/or motor mechanism due to cross-modal SR interactions.

14 Claims, 15 Drawing Sheets

FOREIGN PATENT DOCUMENTS

| | | |
|---|---|---|
| JP | 2006-204520 | 8/2006 |
| WO | 2005/028013 | 3/2005 |

OTHER PUBLICATIONS

Bresciani et al., "Vision and Touch are Automatically Integrated for the Perception of Sequences of Events", Journal of Vision, vol. 16, pp. 554-564, 2006.

Franaszek et al., "Application of Chaotic Dynamics to Stochastic Resonance" Probabillistic Mechanics and Structural Reliabitlity, Proceeding Frangopol, American Society of Civil Engineers, pp. 86-89, 1996.

Gammaitoni et al., "Controlling Stochastic Resonance", Physical Review Letter, The American Physical Society, vol. 8, No. 23, pp. 4574-4577, Jun. 7, 1999.

Gammaitoni et al., "Stochastic Resonance", Reviews of Modern Physics, vol. 70, No. 1, pp. 223-287, Jan. 1998.

Hidaka et al., "Functional Stochastic Resonance in the Human Brain: Noise Induced Sensitization of Baroreflex System", Physical Review Letters, vol. 85, No. 17, pp. 3740-3743, Oct. 23, 2000.

Hidaka et al., "Noise-Enhanced Heart Rate and Sympathetic Nerve Responses to Oscillatory Lower Body Negative Pressure in Human", The Journal of Neurophysiology, vol. 86, pp. 559-564, 2001.

Johnson et al., "Multifocal Spectacles Increase Variability in Toe Clearance and Risk of Tripping in the Elderly", Investigative Ophthamology & Visual Science, vol. 48, No. 4, pp. 1466-1471, Apr. 2007.

Kitajo et al., "Behavioral Stochastic Resonance within the Human Brain", Physical Review Letters, vol. 90, No. 21, pp. 218103-1-218103-4, May 30, 2003.

Laurienti et al., "Enhanced Multisensory Integration in Older Adults", Neurobiology of Aging27, pp. 1155-1163, 2006.

Moss et al., "The Benefits of Background Noise", Scientific American Inc., pp. 66-69, Aug. 1995.

Moss et al., "Stochastic Resonance and Sensory Information Processing: A Tutorial and Review of Application", Clinical Neurophysiology, vol. 115, 2004, pp. 267-281.

Ward et al., "Stochastic Resonance in Psychophysics and in Animal Behavior", Biological Cybernetics, vol. 87, 2002, pp. 91-101.

Dhruv et al., "Enhancing tactile sensation in older adults with electrical noise stimulation", Somatosensory Sytems Pain, NeuroReport, Lippincott Williams & Wilkins, vol. 13, No. 5, Apr. 16, 2002 pp. 597-600.

* cited by examiner

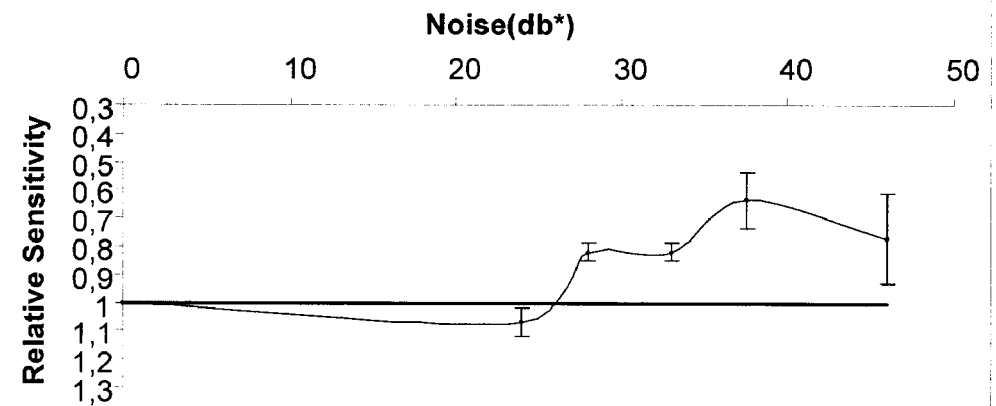
Figure 6a  S7
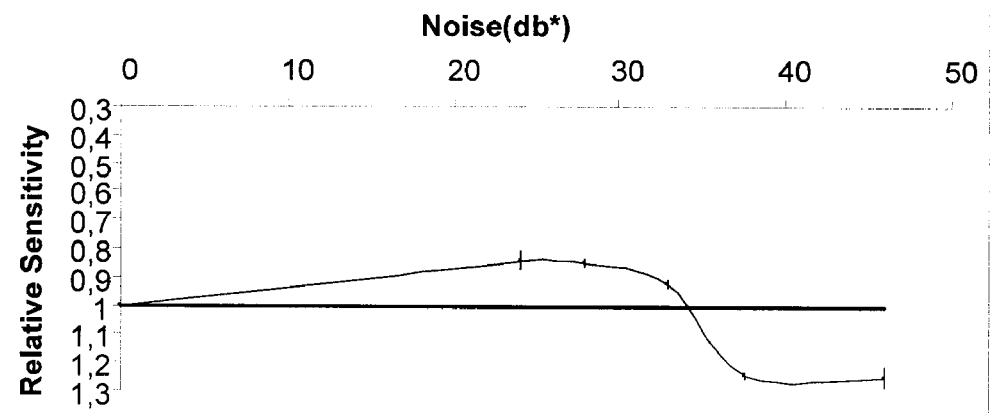
Figure 6b  S8
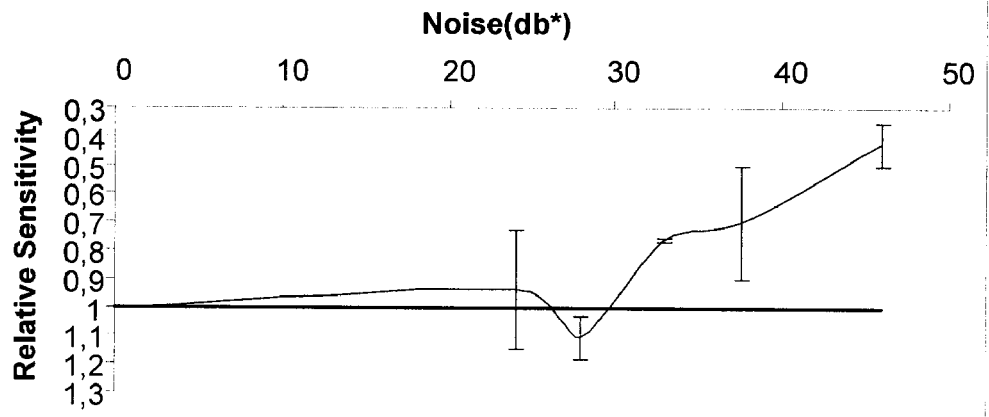
Figure 6c  S15

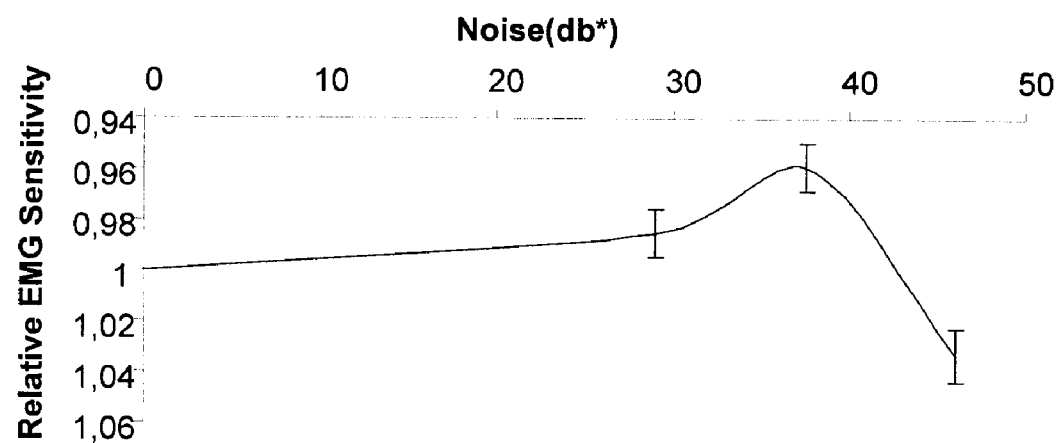
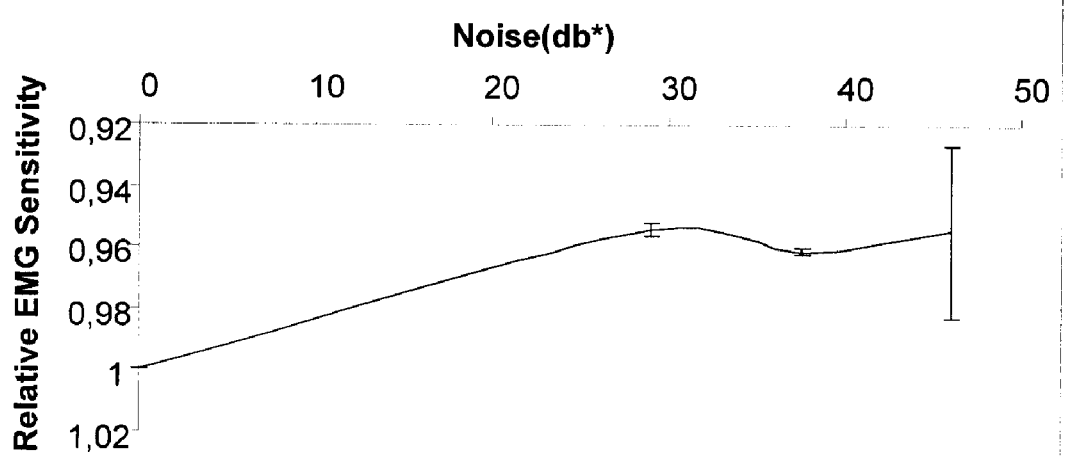

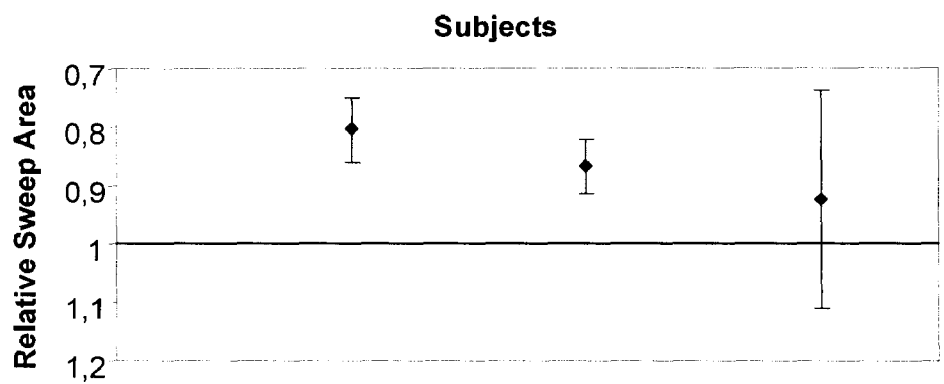
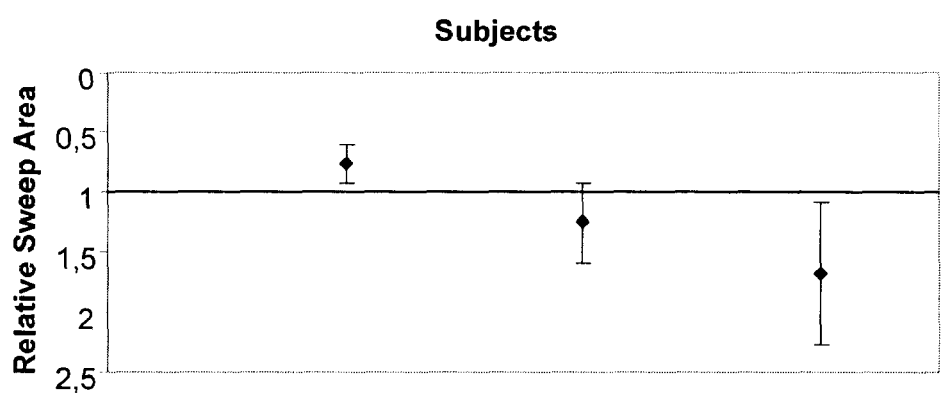
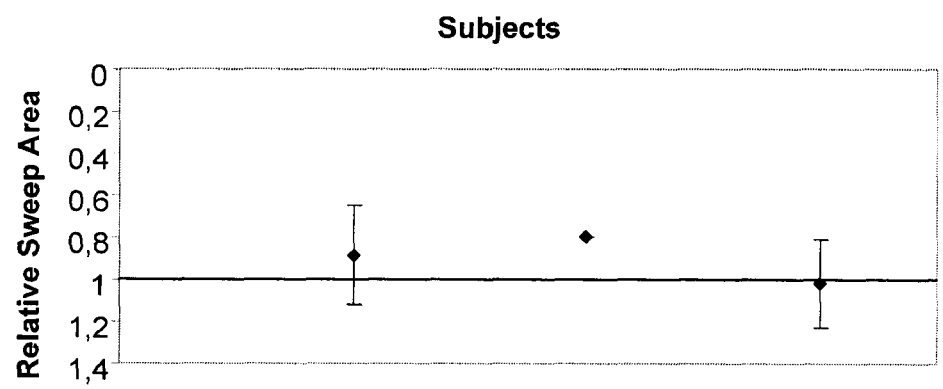

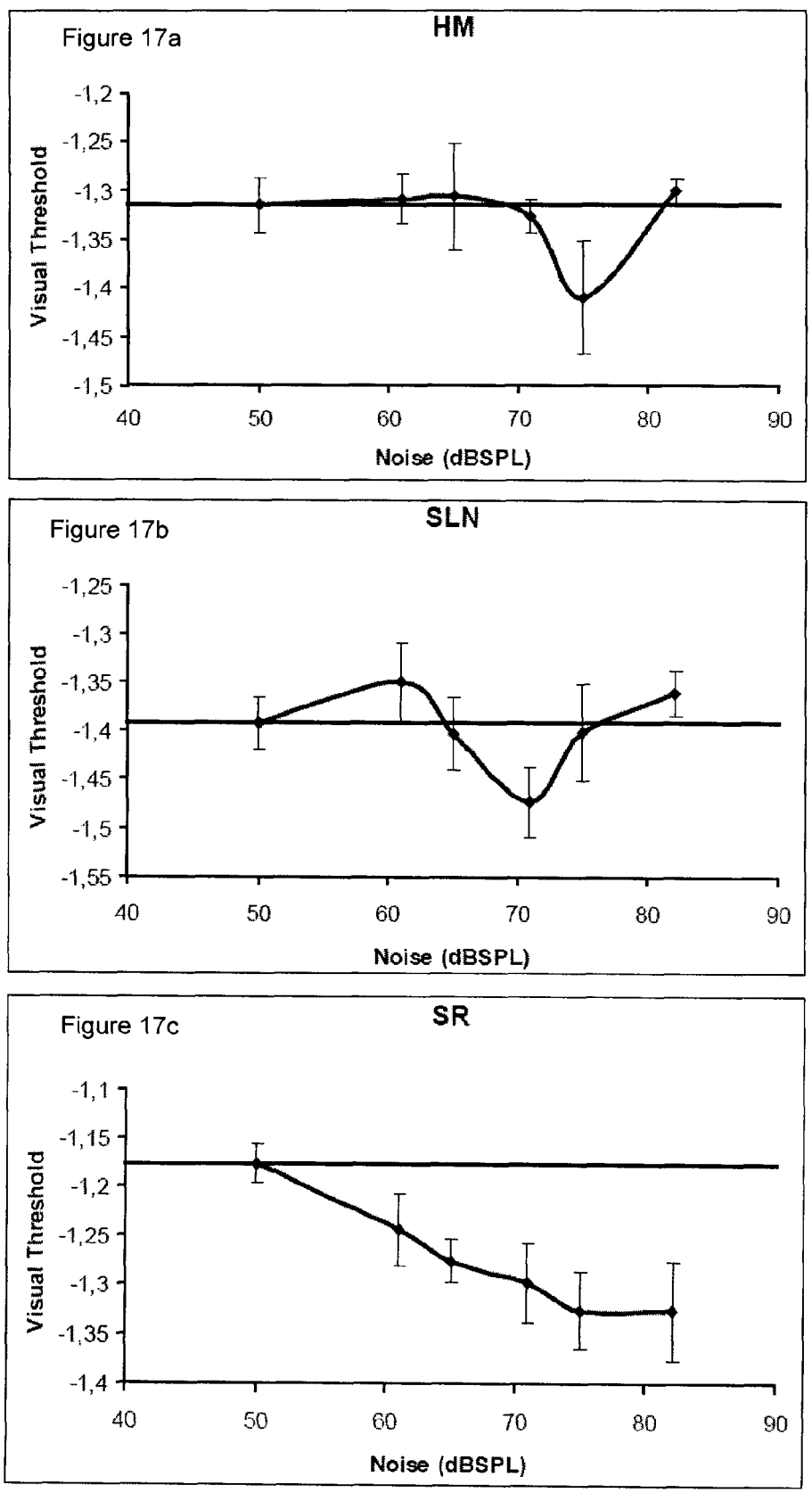

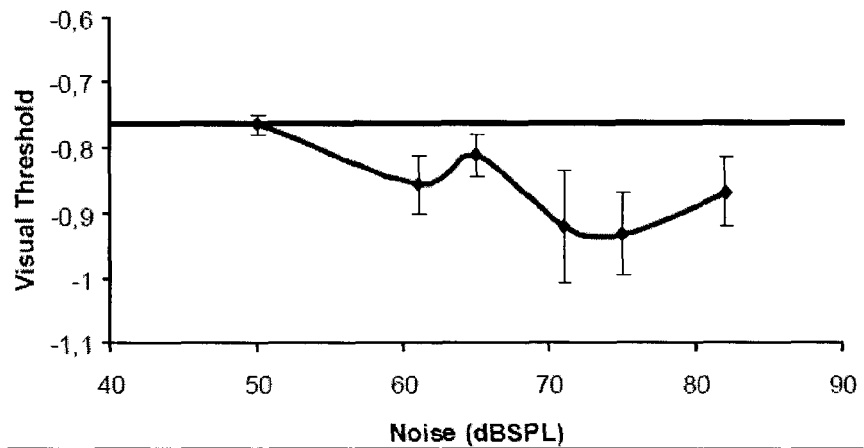
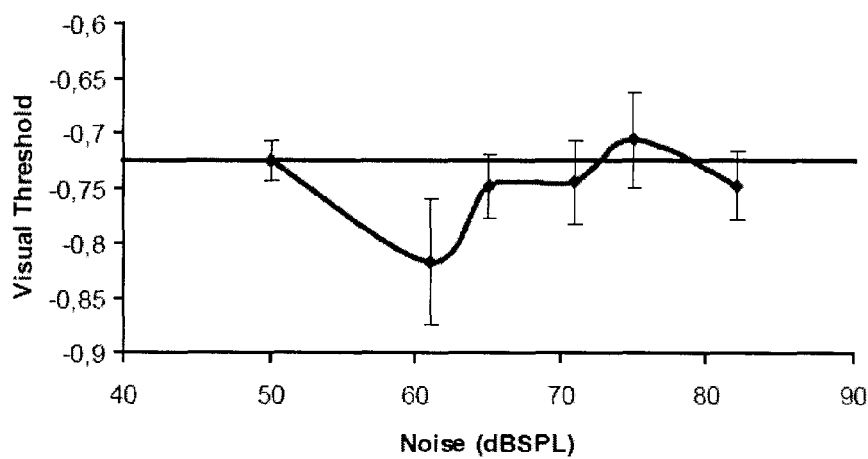
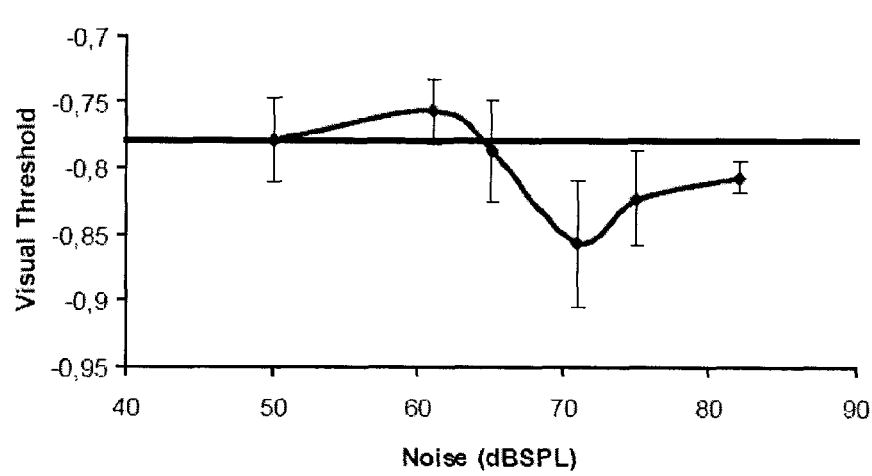

METHOD AND SYSTEM FOR IMPROVING A SUBJECT'S SENSORY, REFLEX AND/OR MOTOR MECHANISMS VIA AUDITORY, TACTILE OR VISUAL STIMULATIONS

FIELD OF THE INVENTION

The present invention generally relates to stimulating a subject's sensory, reflex and/or motor mechanisms using the concept of stochastic resonance. More specifically, but not exclusively, the present invention is concerned with a method and system for improving a subject's sensory, reflex and/or motor mechanisms via sensory stimulations, such as auditory, tactile or visual stimulations.

BACKGROUND OF THE INVENTION

Stochastic Resonance (SR) is a well-known phenomenon that occurs in different macro, micro and even nano systems. SR allows for improving the detectability of a signal below a threshold by injecting a noise into the systems. Therefore, SR appears to be an interesting and attractive phenomenon to be applied in sensory systems in order to improve the sensitivity of the subject's sensory, reflex and/or motor mechanisms.

Indeed, it has been shown that, when a weak sensory stimulus applied to an individual, for stimulating a specific sense, is added with an appropriate amount of white noise, the weak sensory stimulus can then be detected and thus activate the reactions of that particular sense in response to the applied weak sensory stimulus.

For example, in "The Benefits of Background Noise", a paper written by Frank Moss and Kurt Wiesenfeld, for Scientific American Inc., in 1995, the role of SR was investigated in biological sensory systems. For that purpose, the fine hairs in a crayfish's tail were under test. The fine hairs can detect motions, such as water motions caused by the arrival (movement) of a potential predator. In the experimental set-up, a crayfish's tail was isolated and mounted to a post and then placed inside a tank containing a saline solution. Also, an electrode was inserted in the nerve cord connected to the hairs, in order to measure the level of nerve impulses generated by the nerve, in response to the motions of the post detected by the hairs. A random noise was then added to the signal moving the post so as to create fluctuations in the motions of the post. Results showed that the sensitivity of the fine hairs was increased and the results exhibited the SR phenomenon.

It is further suggested in the same paper that SR has practical applications in the field of medical science and more specifically in the nervous system of human beings. In the same way, the paper entitled "Stochastic Resonance in Psychophysics and in Animal Behavior", by L. M. Ward et al., published in Biological Cybernetics, 87, 91-1001, in 2002, states that SR can be used for improving human performance through auditory, visual and tactile sensory systems since they contain a neural system.

Regarding Japanese patent application JP2003048453 A2, entitled "Display Device for Vehicle", by Hirose Satoro, published in 2003, a device is provided for a driver's car for increasing the driver's awareness of the surroundings and for keeping his/her attention focused on the road. To do so, a plurality of embodiments of the device has been developed, using different sensory stimulations, such as a visual, auditory or vibratory stimulation. The different embodiments were installed on the side mirrors of the car, on the steering wheel, etc. Each embodiment comprises a noise generator for producing a noise necessary for improving the perception of the driver according to the SR phenomenon. However, this device is meant for use only with car driving.

In US Patent Application No. 2004/0073271 A1, entitled "Method and System for Neurophysiologic Performance", by J. D. Harry et al., published in 2004, a system for improving neurophysiologic performance is disclosed. The system consists of a garment which comprises at least one input signal device that can be positioned at different locations on the garment, and one signal generator. The input signal device, such as electrodes or muscle stimulators, allows for inputting a bias signal to sensory cells for improving the functions thereof during a physical activity. The bias signal is generated by the signal generator. This system mainly focuses on contact stimulations through the skin.

In US Patent Application No. 2004/0173220 A1, entitled "Method and System for Improving Human Balance and Gait and Preventing Foot Injury", by J. D. Harry et al., published in 2004, a wearable device such as a shoe insert or a sock for shoes is disclosed. The wearable device comprises electrodes and vibratory actuators for producing vibrations so as to stimulate the feet and ankles of an individual. Furthermore, the wearable device also comprises a signal generator for generating a random noise to be added to the vibrations. Using the SR principle, the wearable device allows for improving the gait and balance of the individual. This device is used only for foot stimulations.

So far, it has been shown that the principle of SR can be applied in a uni-modal way, meaning that both the signal and the noise are applied to a same receptor. For example, to enhance the tactile sensitivity, a tactile stimulus and a tactile noise are applied to a tactile mechanism, and to enhance the visual sensitivity, a visual stimulus and associate noise are applied to a visual mechanism.

However, so far, it has never been shown how to stimulate one subject's sensory mechanism with noise to affect another sensory, reflex and/or motor mechanism of the same subject, and how the noise acts upon a multi-sensory integration system.

OBJECTS OF THE INVENTION

Therefore, to overcome the above discussed drawbacks and to complete studies on behavioral SR, an object of the present invention is to show improvement of the sensitivity of a subject's sensory, reflex and/or motor mechanism by stimulating another different sensory mechanism and the action of a noise in a multi-sensory integration mechanism.

Another object of the present invention is to provide a method and system for improving a subject's sensory, reflex and/or motor mechanisms via auditory, tactile or visual stimulations.

SUMMARY OF THE INVENTION

More specifically, in accordance with the present invention, there is provided a method for improving sensitivity of a first sensory, reflex and/or motor mechanism of a subject, comprising stimulating a second sensory, reflex and/or motor mechanism of the subject. Stimulating the second sensory, reflex and/or motor mechanism of the subject comprises applying a noise to the second sensory, reflex and/or motor mechanism, and applying a noise to the second sensory, reflex and/or motor mechanism improves the sensitivity of the first sensory, reflex and/or motor mechanism due to cross-modal SR interactions.

The present invention also relates to a system for improving sensitivity of a first sensory, reflex and/or motor mechanism of a subject, comprising a source of a stimulation signal and a stimulator responsive to the stimulation signal and producing, in response to the stimulation signal, a noise applied to a second sensory, reflex and/or motor mechanism of the subject. Application of the noise to the second sensory, reflex and/or motor mechanism improves the sensitivity of the first sensory, reflex and/or motor mechanism of a subject due to cross-modal SR interactions.

The foregoing and other objects, advantages and features of the present invention will become more apparent upon reading of the following non-restrictive description of an illustrative embodiment thereof, given by way of example only with reference to the accompanying drawings.

BRIEF DESCRIPTION OF THE DRAWINGS

In the appended drawings:

FIGS. 6a, 6b and 6c are graphs illustrating the relative sensitivity of three subjects as a function of noise, wherein 0 db* equals 0.218 mV peak;

FIGS. 9a, 9b, 9c and 9d are graphs illustrating the relative electromyography (EMG) sensitivity of four subjects as a function of noise;

FIGS. 11a, 11b, and 11c are graphs illustrating a relative sweep area of three (3) subjects as a function of noise, wherein the area is calculated from the 95% confidence ellipse area from stabilograms;

FIGS. 17a, 17b and 17c are graphs illustrating results related to a fifth example of application of the system for stimulating a subject; and FIGS. 18a, 18b and 18c are graphs illustrating results also related to the fifth example of application of the system for stimulating a subject.

DETAILED DESCRIPTION

Figure 1:
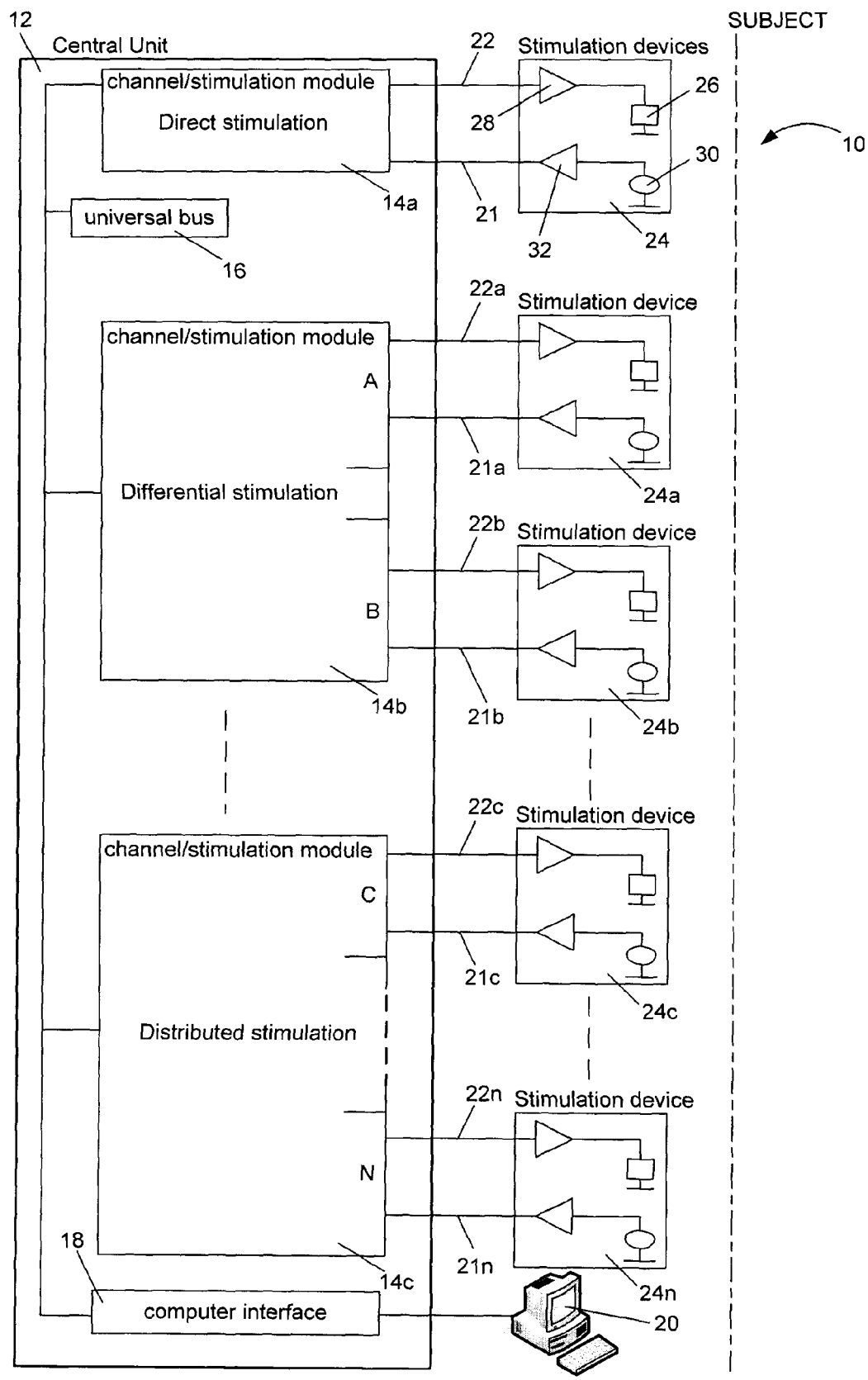
FIG. 1 represent a schematic block diagram illustrating a system for stimulating a subject according to the non-restrictive illustrative embodiment of the present invention.

The non-restrictive illustrative embodiment of the present invention, as shown by the block diagram of FIG. 1, uses the concept of SR for improving a subject's sensory, reflex and/or motor mechanisms, more specifically the general sensitivity and postural balance of the subject.

For SR to occur in a non linear system, the non linear system needs three (3) parameters: (i) a threshold, (ii) noise and (iii) subthreshold information, wherein the subthreshold information relates to a signal or stimulus applied to a sensory mechanism and having too low a magnitude (below a threshold) to allow the sensory mechanism to react to that stimulus. In fact, SR is a non linear phenomenon whereby addition of a noise, for example a white noise, can improve detection of the subthreshold information by enhancing the information content. However, only an optimal amount of added noise can yield an optimal enhancement of the detection. Indeed, when too small a noise is added, the subthreshold information is still below the threshold and cannot be detected. When too strong a noise is added to the stimulus, the noise becomes too strong with respect to the information content of the stimulus and, therefore, this too strong a noise will randomize the reactions of the subject's sensory, reflex and/or motor mechanisms in response to the stimulus.

A non limitative aspect of the non restrictive illustrative embodiment of the present invention is concerned with stimulating a particular type of sensory mechanism of a subject to improve another type of sensory, reflex and/or motor mechanism of the same subject. Experiments have shown that applying an auditory noise to the ear(s) of a subject modulates the tactile sensation of his/her index finger, modulates the EMG activity of his/her leg muscles and/or modulates the stabilogram sweep area during posture maintenance. Therefore, these experiments show that interactions inside the human cortex are cross-modal SR based interactions, which form a multi-sensory integrated system. Under the influence of a noise in the multi-sensory integrated system, the generalized state of a subject can be enhanced, including the postural balance.

First a system according to the non restrictive illustrative embodiment of the present invention, for improving a subject's sensory and balance mechanisms via auditory or visual stimulations will be described. Then, examples will be presented and discussed in detail.

Description of the System for Improving Sensory and Balance Mechanisms Via Auditory, Tactile or Visual Stimulation Referring to FIG. 1, a system 10 for producing one or a plurality of stimuli to be applied to a subject is illustrated in FIG. 1. The system 10 comprises a plurality of units connectable to each other, wherein these units can be static or portable.

The system 10 first comprises a central unit (CU) 12, which includes a plurality of channel/stimulation modules such as 14. The plurality of channel/stimulation modules 14 are interconnected through a universal bus 16, which is also connected to an interface 18 through which a computer such as 20 can access and manage the CU 12. Furthermore, each channel/stimulation module 14 is provided with one or several pairs of input-output ports 21 and 22 for connecting one or several stimulation devices 24 thereto. The stimulation devices 24 can be of different types, such as vibrators, headphones, displays, etc.

The CU 12 can be provided with data acquisition capabilities so that the CU 12 can process data generated in the channel/stimulation modules 14. Or, alternatively, for further processing of the data, the CU 12 may be connected to the computer 20 through the interface 18. For example, the computer 20 will then collect and store parameters and/or results of a stimulation process for further analyses. The CU 12 can be a general microprocessor (not limited to electronics: can be optical or biologic) and is advantageously small, light and portable. Central units are otherwise well known to those of ordinary skill in the art and, for that reason, will not be further described in the present specification.

Figure 2:
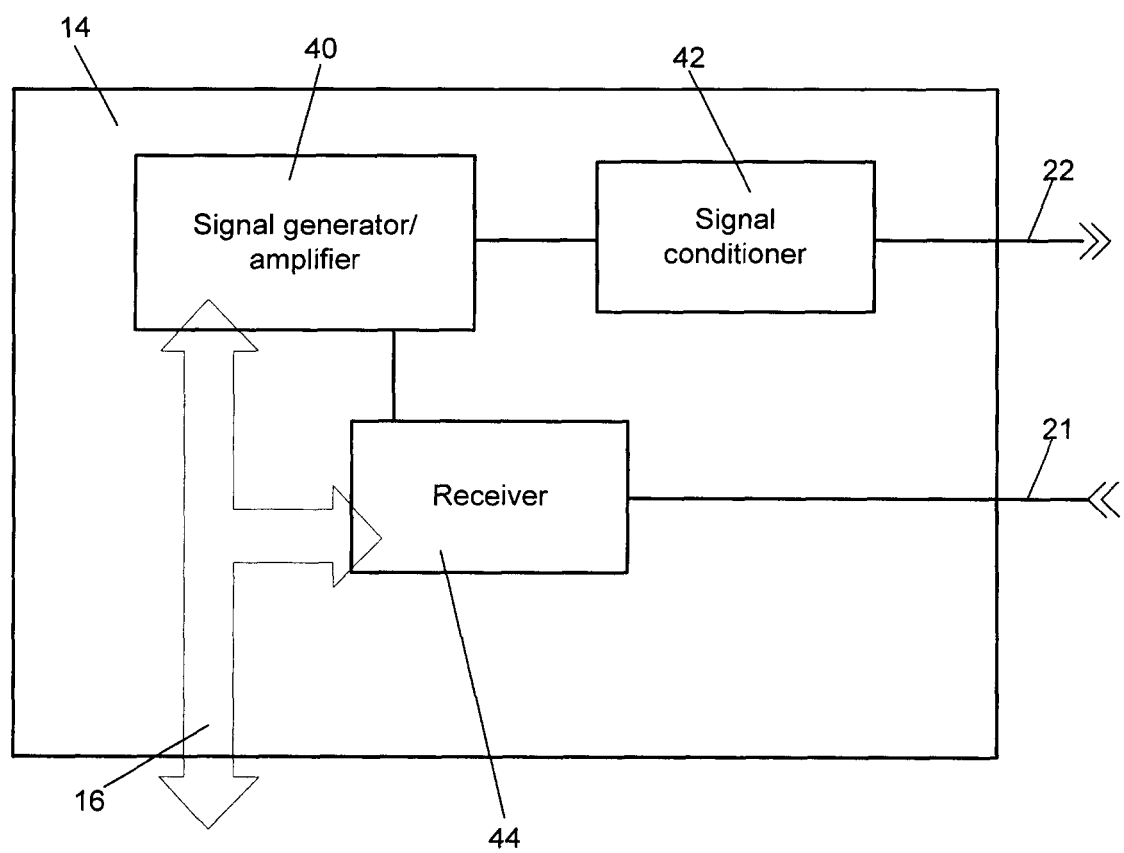
FIG. 2 is a schematic block diagram illustrating one channel/stimulation module of the system of FIG. 1.

As illustrated in FIG. 2, each channel/stimulation module 14 is in fact a signal source and comprises, for example, an amplifier or generator 40 for producing a signal for use in the stimulation process. The amplifier or generator 40 is connected to a signal conditioner 42 for converting the signal from source 40 into a stimulation signal having specific characteristics related to the desired type of stimulation and supplied on the output port 22. At least one stimulation device (stimulator) 24 is connected to every channel/stimulation module 14 via its input-output ports 21 and 22. Each channel/stimulation module 14 also comprises a receiver 44 for receiving signals from the corresponding stimulation device 24 through the input port 21. Signal generators, signal amplifiers, signal conditioners and receivers are otherwise well known to those of ordinary skill in the art and, for that reason, will not be further described in the present specification.

Non limitative examples of signal conditioning include modulation, conversion of analog signals to digital signals, change of the amplitude, frequency, phase or shape of a signal, etc. (Note: electric systems are more common but in this case we could also use mechanics, light, fluids or many other physics means to achieve the function.)

Depending on the complexity of the stimulation process, different types of channel/stimulation modules 14 can be provided. As a non-limitative example, there are provided three (3) different types of channel/stimulation modules 14 as illustrated in FIG. 1.

The first type is a channel/stimulation module 14a dedicated to direct stimulation, wherein the input-output ports 21 and 22 of the channel/stimulation module 14a are connected to a single stimulation device 24 adapted to stimulate a particular area of the subject's body to thereby stimulate a given sensory mechanism of the subject.

The second type is a channel/stimulation module 14b dedicated to differential stimulation, wherein two different areas of the subject's body are used to stimulate a region between these two body areas to thereby stimulate a given sensory mechanism of the subject. Therefore, the channel/stimulation module 14b comprises two pairs of input-output ports 21a-22a and 21b-22b, which are connected to two (2) stimulation devices 24a and 24b, respectively. The two (2) stimulation devices 24a and 24b are designed to apply a same family of stimulations to the above mentioned region between the two (2) body areas corresponding to the stimulation devices 24a and 24b, respectively. Families of stimulators, and therefore the families of stimulations will be defined in the following description.

The third type is a channel/stimulation module 14c is dedicated to distributed stimulation, wherein several areas of the body of the subject are used to stimulate a region of the subject's body covered by these areas to thereby stimulate a given sensory mechanism of the subject. Distributed stimulation enhances stimulation resolution. In this case, the channel/stimulation module 14c is connected to a plurality of stimulation devices 24c to 24n all designed to apply a same family of stimulations. The channel/stimulation module 14c therefore comprises a plurality of pairs of input-output ports 21c-22c to 21n-22n. The different signals generated by the channel/stimulation module 14c on the different input-output ports 21c-22c to 21n-22n can be adjusted as required to obtain the required stimulation, for example by adjusting their characteristics such as intensity and simultaneity.

As a non limitative example, the channel/stimulation module 14c can be designed for stimulating a region of a muscle.

The structure of a stimulation device 24 to apply a stimuli to a subject will now be described. More specifically, each stimulation device 24 generally comprises the same basic components. In the example of FIG. 1, the stimulation device 24 comprises an activator 26 connected to an activator interface 28, itself connected to the output port 22 of the channel/stimulation module 14. The stimulation device 24 also comprises a sensor 30 connected to a sensor interface 32, itself connected to the input port 21 of the channel/stimulation module 14.

It is worth noting that the activator interface 28 or the sensor interface 32 can be a port or any other type of connection devices, and/or they can also comprise an amplifier for amplifying respective signals transmitted through them.

The activator 26 can comprise a transducer (not shown) for converting, for instance (Note: electric systems are more common but in this case we could use mechanics, light, fluids or many other physics means to achieve the function), the electrical signal received through the interface 28 into a stimulus, such as heat, vibrations, light, sound, etc., corresponding to the type of stimulus that the activator 26 is designed to apply. Such transducers are otherwise well known to those of ordinary skill in the art and, for that reason, will not be further described in the present specification.

Sensors such as 30 detect and measure different parameters. They can be electrical, electronic or of any other types. They can be designed to detect signals of different categories such as, for example, electric signals, sound, magnetic fields, vibrations, heat, etc. Sensors are otherwise well known to those of ordinary skill in the art and, for that reason, will not be further described in the present specification.

Since the system 10 allows for performing many types of stimulations, the plurality of stimulation devices 24 can be classified into different families or categories of stimulators, according to the type of stimulus to be provided by the stimulation device 24.

Figure 3:
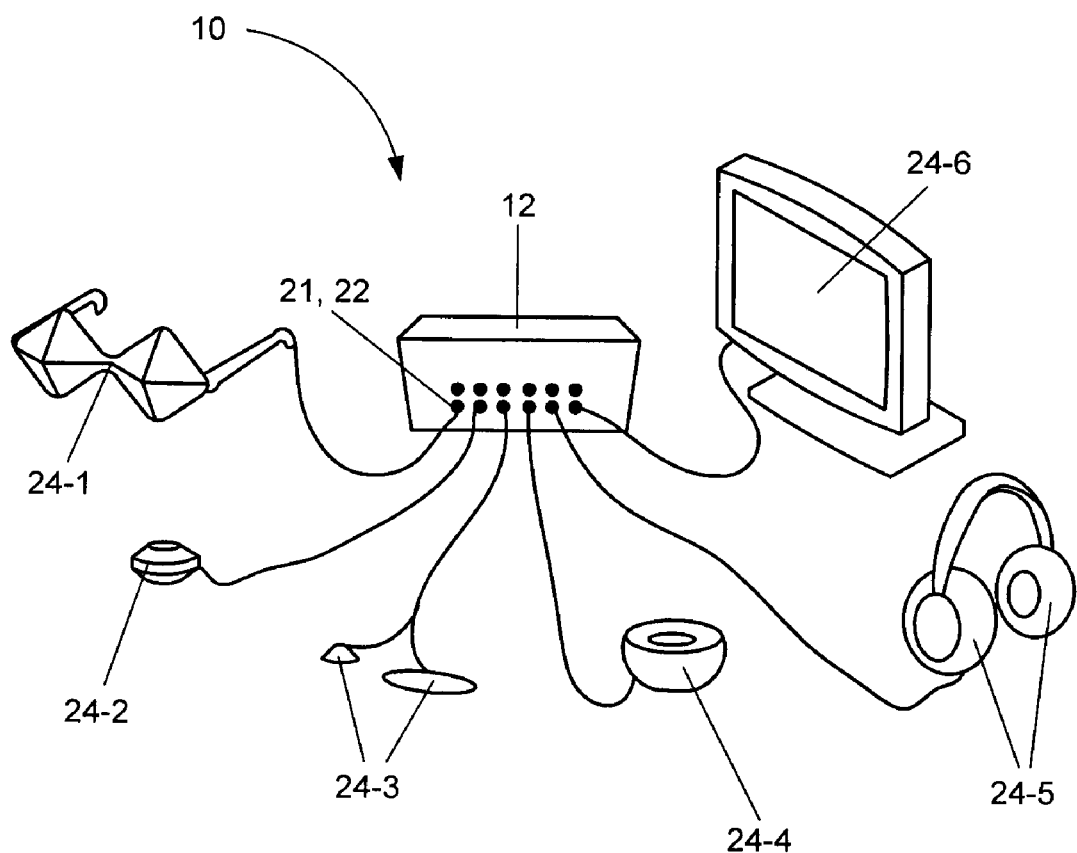
FIG. 3 is an example of physical system for stimulating a sensory mechanism of a subject.

Turning now to FIG. 3, different families of stimulation devices 24 are illustrated. Each stimulation device 24 is connected to the CU 12 through the plurality of ports 21 and 22 of the channel/stimulation modules 14.

A first non limitative example of a family of stimulation devices 24 is given by a visual stimulation device 24-1, 24-6. The visual stimulation device 24-1, 24-6 introduces a visual stimulus in at least one eye of the subject. The visual stimulus can be a blinking light, some light spots changing intensity, or any other visual signal that can stimulate the eye(s) of the subject. Depending on the amplitude of the visual stimulation signal, the subject will or will not detect the signal. The visual stimulation device 24-1, 24,6 comprises as activator 26 either a pair of glasses, in the case of visual stimulation device 24-1, or a display, in the case of visual stimulation device 24-6, each incorporating the sensor 30. The amplitude of the visual stimulus is measured through the sensor 30.

A second non limitative example of a family of stimulation devices 24 is given by a vibratory stimulation device 24-2. The vibratory stimulation device 24-2 applies as stimulation a vibration to an area of the subject's body to thereby stimulate a given sensory mechanism of the subject. Depending on the amplitude of the vibratory stimulation signal, the individual will or will not detect the signal. The stimulation device 24-2 can comprise as activator 26 any type of vibrators also incorporating the sensor 30. The amplitude of the vibratory stimulus is measured by the sensor 30.

A third non limitative example of a family of stimulation devices 24 is given by an electromagnetic stimulation device 24-3. The electromagnetic stimulation device 24-3 produces and applies an electromagnetic field, a controlled current or voltage to an area of the subject's body to thereby stimulate a given sensory mechanism of the subject. Depending on the amplitude of the electromagnetic stimulation, the subject will or will not detect the stimulation. The stimulation device 24-3 can comprise as activator 26 electromagnetic radiation emitting coils or antennas also incorporating the sensor 30. The amplitude of the electromagnetic field is measured through this sensor 30.

A fourth non limitative example of a family of stimulation devices 24 is given by a thermal stimulation device 24-4. The thermal stimulation device 24-4 produces and applies heat as stimulation to an area of the subject's body to thereby stimulate a given sensory mechanism of the subject. Depending on the amplitude of the thermal stimulation signal applied to the subject's body, the subject will or will not detect the signal. The thermal stimulation device 24-4 can comprise as activator 26 any type of electrical heaters also incorporating the sensor 30. The amplitude of the thermal stimulus is measured through this sensor 30.

Finally, a fifth non limitative example of a family of stimulation devices 24 is given by an acoustic stimulation device 24-5. The acoustic stimulation device 24-5 produces and applies to the subject's body a vibratory energy spectrum and/or an acoustic energy spectrum, for example to at least one ear of the subject. Depending on the amplitude of the acoustic stimulation signal, the subject will or will not detect the signal. The acoustic stimulation device 24-5 can comprise, as a non limitative example of activator 26, speaker(s) or headphone(s) incorporating the sensor 30. The amplitude of the acoustic stimulus is measured by the sensor 30.

The general operation of the system 10 will now be described with reference to FIG. 1. For purposes of simplicity and clarity, the operation of the system 10 will be described in relation to a single stimulation and a single channel/stimulation module 14 carrying out that stimulation. Those of ordinary skill in the art will appreciate that it is possible to extend the operation of the system 10 to several, simultaneous stimulations using the required number of channel/stimulation modules 14 and stimulations devices 24.

An operator first selects a desired type of stimulation such as, for example, a visual stimulation, an acoustic stimulation, a vibratory stimulation, etc. Then, the operator connects a stimulation device 24, corresponding to the selected type of stimulation, to the CU 12 via the appropriate input-output ports 21 and 22. By so doing, the CU 12 automatically establishes links between the stimulation device 24 and the corresponding channel/stimulation module 14.

The operator then activates the CU 12, for example through depression of a push-button or key, to instruct via the bus 16 the signal generator 40 (FIG. 2) to generate a stimulation signal. The stimulation signal from the generator 40 is then processed through the signal conditioner 42 and supplied to the stimulation device 24 through the output port 22.

The stimulation signal received by the stimulation device 24 is supplied to the activator 26 through the activator interface 28. Once the activator 26 receives the stimulation signal, the activator 26 converts it into a stimulus such as light, vibrations, sound, etc. Once the stimulation signal is converted into a stimulus, it is applied to the subject's sensory mechanism and simultaneously detected and measured by the sensor 30.

Once the stimulation signal is detected, the sensor 30 formed by a transducer converts the detected stimulation signal back into an electrical signal that is transmitted back to the channel/stimulation module 14 via the sensor interface 32 and the input port 21. The electrical signal is received by the receiver 44 and analyzed by the CU 12. For example, the amplitude of the received signal is retrieved. By depressing the same or another push-button or key, the operator can instruct the CU 12 to produce and transmit another command, via the bus 16, to the signal generator 40 to generate another stimulation signal, with the same of different characteristics, for repeating the stimulation process.

This loop constitutes a closed-loop control allowing for continuous evaluation of the intensity and other characteristics of the stimulation signals.

Figure 4:
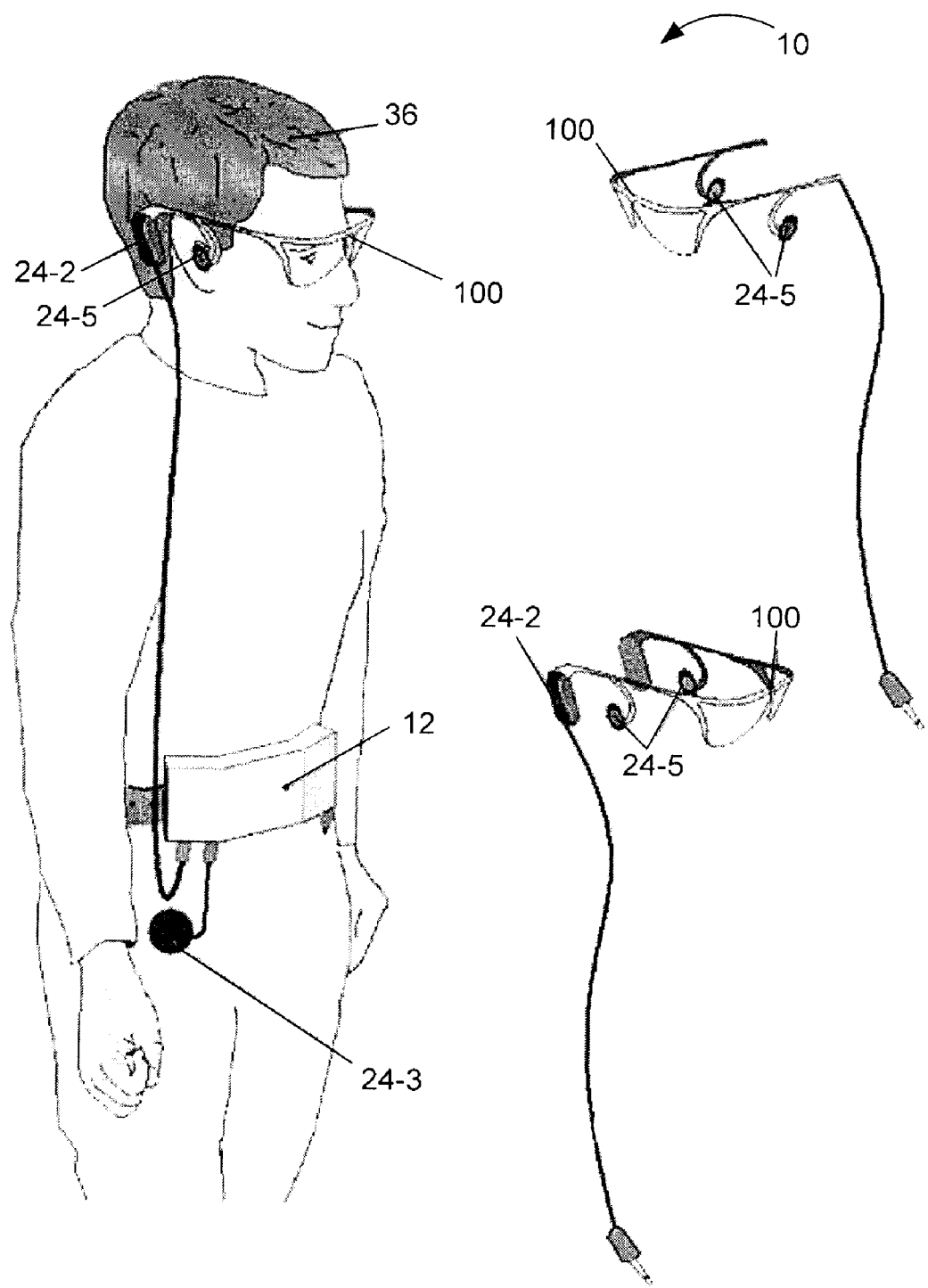
FIGS. 4 and 4a are schematic illustrations of a subject under the influence of two simultaneous sensory simulations using the system of FIG. 1.

The system 10 as shown in FIG. 4 is very flexible with regards to the number of stimulations. It is also easy to operate and can be easily transported by a person.

Figure 4A:
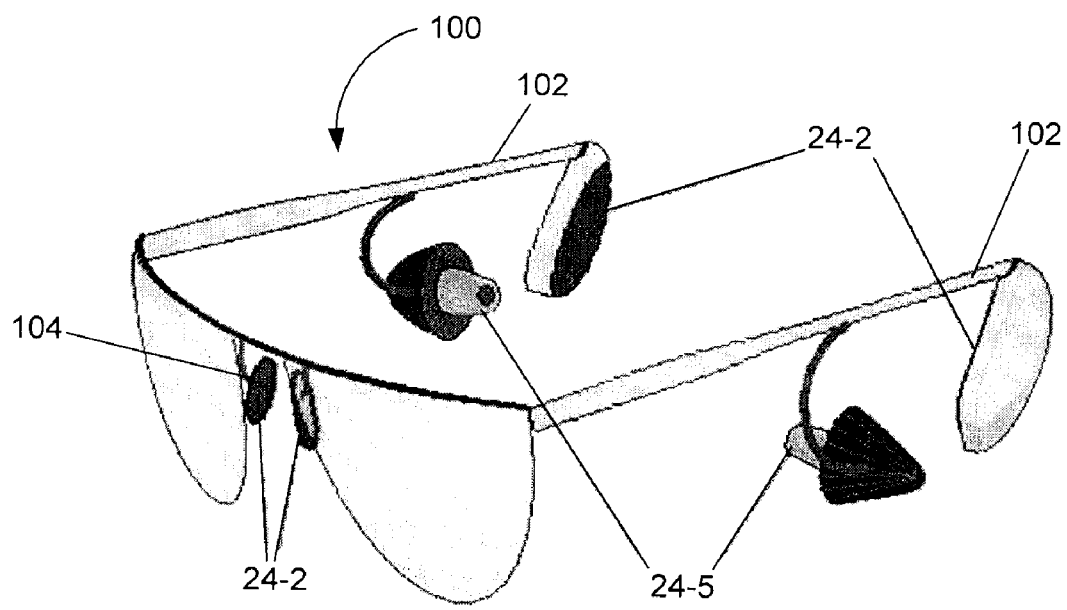

More specifically, the example of system 10 as illustrated in FIG. 4 simultaneously generate different stimulations. A subject 36 wears the central unit 12 on a belt fixed around his waist. A first stimulation device 24-5 in the form of an acoustic stimulation device, a second stimulation device 24-3 in the form of an electromagnetic stimulation device and a third stimulation device in the form of vibrators 24-2 are connected to the central unit 12. The device 24-5 comprises, for example, a pair of earphones mounted on spectacles 100. As shown more clearly in FIG. 4a, the vibrators 24-2 can be mounted on the distal end of the ear stems 102 and on the nose pads 104 of the spectacles 100. The system 10 of FIG. 4 was used to demonstrate that tactile sensitivity of the subject 36 can be improved via acoustic stimulation. The system 10 of FIG. 4 could also be used to demonstrate that tactile sensitivity of the subject 36 can be improved via stimulation of the subject through the vibrators 24-2.

Figure 5:
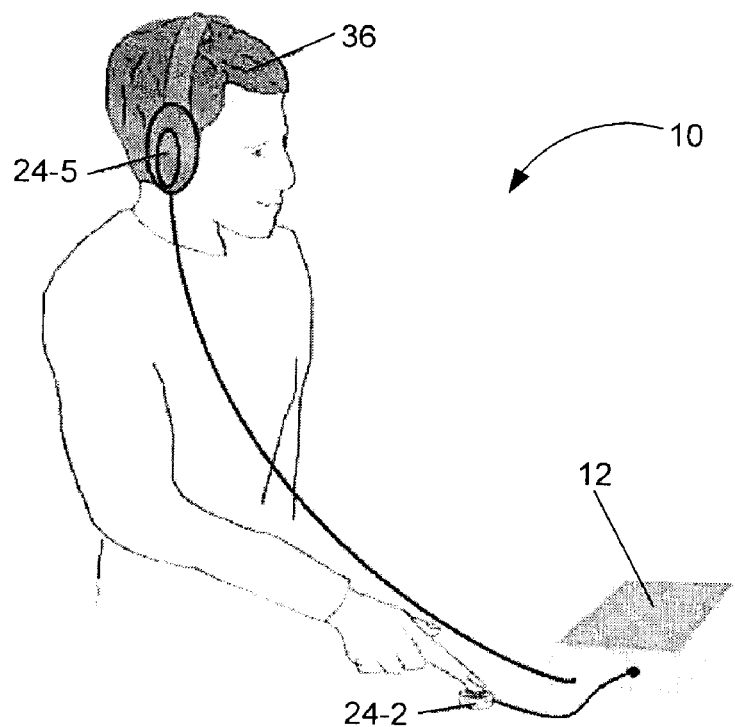
FIG. 5 is another schematic illustration of a subject under the influence of two simultaneous sensory simulations using the system of FIG. 1.

Another example is given in FIG. 5, where the subject 36 is under the influence of two stimulations simultaneously applied by the acoustic stimulation device 24-5 and the vibratory stimulation device 24-2. For example, the set-up of FIG. 5 was used to demonstrate that tactile sensitivity of the subject 36 can be improved via acoustic stimulation.

Of course, it should be understood that many other such combinations of stimulations are possible, with two (2) or even more simultaneously applied stimuli.

In order to apply the principle of cross-modal SR, when the subject 36 is under the influence of several stimulations, one of the stimulations is provided with noise for improving the sensitivity of the other stimulations. For example, for improving the tactile sensitivity as illustrated in FIG. 5, the subject 36 is provided with an acoustic noise, whose intensity can be adjusted by the subject 36. Adjustment of the acoustic noise allows for finding the optimal level of improvement of the tactile sensitivity. The procedure will be described in more detail herein below.

Therefore, the system 10 can help improve, for example, general sensitivity and postural balance especially, but not exclusively, for people who are going through neuromuscular rehabilitation and re-adaptation, for people who have been burned, who have postural problems or skin sensitivity problems, who do sport activities, who are diabetic, for elderly people, etc.

In another example, the system 10 may help elderly people because despite the decline in sensory processing that accompanies aging, the use of multiple sensory channels may represent an effective compensatory strategy to overcome these unisensory deficits. However, it is possible to envisage that any neurobiological alterations such as Alzheimer's, Parkinson's disease, autism and persons with brain injuries could profit of such an approach.

Now, the above mentioned experiments, which were performed to show that SR is a cross-modal phenomenon occurring in human cortex interactions, will be described herein below.

FIRST EXAMPLE

A first example will be described with reference to FIG. 5. More specifically, the first example is concerned, in particular but not exclusively, with the investigation of the effects of, for example, an auditory noise on tactile sensitivity of the subjects. For that purpose, three (3) subjects, namely S7, S8 and S15, were chosen in order to determine and measure the pattern of their respective tactile threshold in the presence of auditory noise.

FIG. 5 shows one 36 of the subjects under stimulation. The age of the three (3) subjects ranges from 35 to 50 years. The system 10 is used to perform two simultaneous stimulations: (i) a tactile-vibratory stimulation provided by the vibratory stimulation device 24-2, and (ii) an acoustic stimulation provided by the acoustic stimulation device 24-5 formed by headphones.

The vibratory stimulation device 24-2 was controlled and monitored by the CU 12 and vibrated with an amplitude of 0.1 to 130 microns in a steady state regime. More specifically, the vibratory stimulation signal was applied to the tip of the index finger of the subjects' right hand at a rate of 100 Hz.

In a first step, the three (3) subjects such as subject 36 were asked to adjust the amplitude of the vibrations from the vibratory stimulation device 24-2 just under the threshold of sensitivity. To do so, at the beginning, a strong vibratory stimulation was applied to the subject's index finger, so that the vibrations can be felt by the subject. Then, the strength of the vibratory stimulation signal was slowly decreased until the subject no longer sensed the vibrations. This level of vibration therefore yielded subthreshold level of stimulation. Once the subthreshold level had been determined, the amplitude of the vibratory stimulation signal was set to that level for the rest of the experiment.

In a second step, the three (3) subjects such as subject 36 were subjected to an auditory noise through the headphones 24-5. The subject was then asked to indicate, by yes or no, whether he/she sensed the subthreshold vibratory stimulations while listening to the auditory noise produced through the headphones 24-5. Listening to the auditory noise did allow the subjects such as subject 36 to sense the subthreshold vibrations even though the amplitude of these vibrations was lower that their tactile threshold. The auditory stimulus was a noise for example an electronically amplified digital noise generated through a suitable noise generator.

In this first example, the tactile sensitivity threshold of the three (3) subjects such as subject 36 was measured with six (6) different noise conditions. The first noise condition was simply the absence of noise and the following four (4) noise conditions were increasing levels of noise, with the noise being produced through the headphones 24-5.

Results are shown in FIGS. 6a, 6b and 6c, which are graphs of the relative tactile sensitivity as a function of the noise (db*) with the no-noise condition used as reference. The three (3) curves of the graphs of FIGS. 6a, 6b and 6c correspond to the three (3) subjects, respectively, and generally exhibit a similar behavior. As the noise level increases, the relative tactile sensitivity of the subjects also increases until it reaches a maximum, after which the relative tactile sensitivity decreases back to the reference point or even lower, even though the level of noise continues to increase. As can be seen, the three (3) curves exhibit the typical signature of the SR phenomenon.

It should be noted that the maximum of relative tactile sensitivity of the three (3) subjects such as subject 36 is not given by the same level of noise, as can be seen in FIGS. 6a, 6b and 6c. Therefore, the variation in the maximum value of tactile sensitivity indicates that the optimal level of noise for achieving the maximum effect from the SR phenomenon is specific to each individual. This means that each subject has different auditory and tactile thresholds which depend on factors such as, for example, age, health or other predispositions.

SECOND EXAMPLE

In this second example, fourteen (14) subjects were chosen, whose age ranged from 25 to 51 years. The set-up was the same as that of the first example as illustrated in FIG. 5. The fourteen (14) subjects were asked to sense a subthreshold vibratory stimulation under the influence of an auditory noise, for example a white noise. However, this second example used only two noise conditions: the no-noise condition and a constant noise condition. More specifically, the constant noise condition was set to a level of 33 db*.

Figure 7:
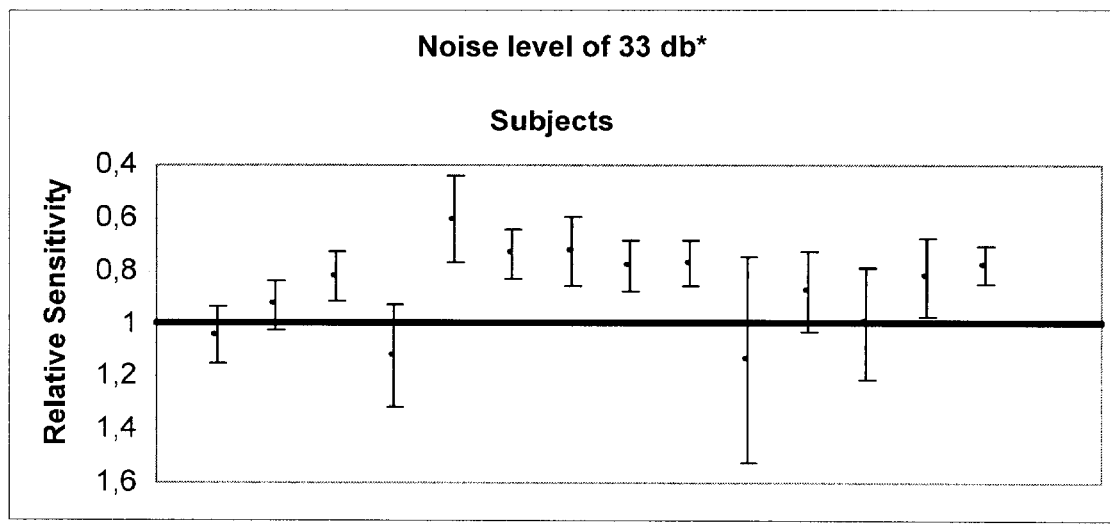
FIG. 7 is another graph illustrating the relative sensitivity of fourteen subjects as a function of noise.

Results related to this second example are presented in the graph of FIG. 7. More specifically, this graph shows the relative tactile sensitivity of the fourteen (14) subjects as a function of the constant noise condition of 33 db* and with the no-noise condition being used as reference. In FIG. 7, it can be seen that ten (10) out of the fourteen (14) subjects, that is 71% of the subjects, saw their relative tactile sensitivity increase in the presence of an auditory noise. Although four (4) subjects saw their relative tactile sensitivity decrease in the presence of an auditory noise, FIG. 7 shows that these particular events are within the error margins (see vertical lines crossing the reference line); this means that the results for these four (4) subjects can be statistically assimilated to the reference line. However, the fact that these four (4) subjects did not show a significant increase of their relative tactile sensitivity from the reference line can be due to the fact that the noise level was not optimized for these four (4) subjects. As demonstrated by the first example, an optimal level of auditory noise can be found for each subject and this optimal level of auditory noise can be different from one subject to the other due to factors such as age, health conditions, etc.

THIRD EXAMPLE

The third example has shown that the SR phenomenon is a generalized sensory phenomenon. The third example is concerned with EMG responses of the leg muscles of different subjects during posture maintenances while the subjects are stimulated by an auditory noise.

Figure 8:
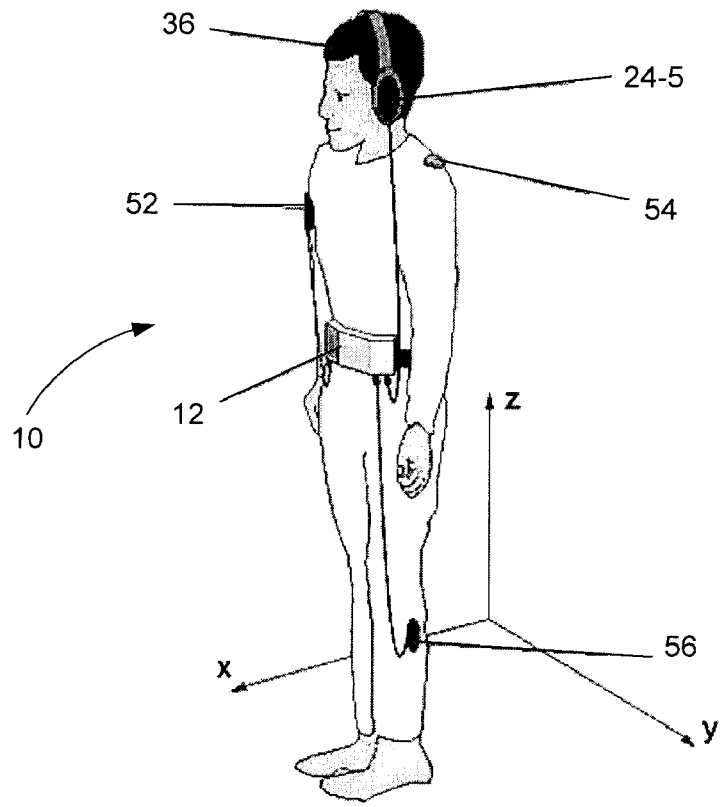
FIG. 8 is a further illustration of a subject under the influence of two simultaneous simulations using the system of FIG. 1.
Figure 9A:
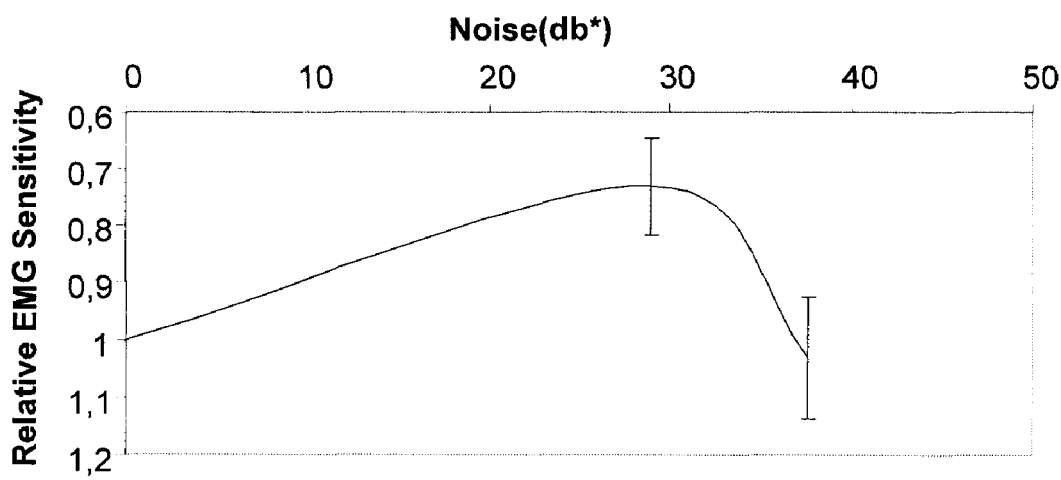
Figure 9B:
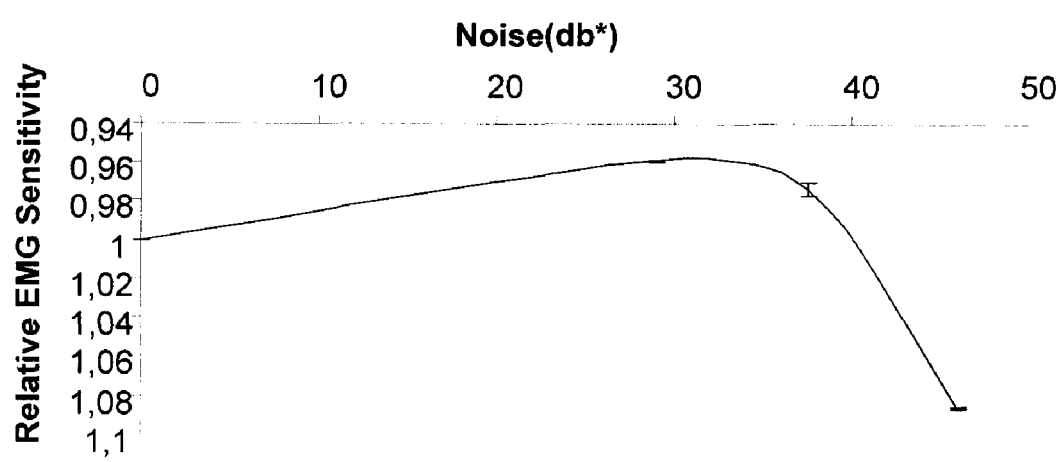

The set-up for this third example is illustrated in FIG. 8. As can be seen, the set-up of FIG. 8 is similar to the set-ups used for the first and second examples. Referring to FIG. 8, the CU 12 is connected to an acoustic stimulation device 24-5, an electromagnetic stimulation device 24-3 (not shown in FIG. 8 but illustrated in FIG. 4), an EMG reference 52, a position sensor 54 and an EMG sensor 56. A group of four (4) subjects such as subject 36, namely S3, S6, S7 and S8, were chosen. The EMG response was measured for the four (4) subjects by applying a tactile electromagnetic stimulation from the electromagnetic stimulation device 24-3 to a foot or a calf of the subjects.

In the same manner as described hereinabove in relation to the first example, an EMG subthreshold amplitude was first determined by using the system 10 as illustrated in FIG. 8. Then, an auditory noise, for example a white noise, was produced and supplied to the subjects through the headphones 24-5 while recording the EMG. Several noise conditions (intensity) were tested.

Results related to the third experiment are reported in the graphs of FIGS. 9a, 9b, 9c and 9d, in which the no-noise condition is taken as the reference. More specifically, the graphs of FIGS. 9a, 9b, 9c and 9d show the relative EMG sensitivity as a function of the noise level. The relative EMG sensitivity was inferred from the power spectrum density of the EMG activity of the right foot's sole for subject S3 and of the right calf for subjects S6, S7 and S8. As can be seen in FIGS. 9a, 9b, 9c and 9d, the typical SR signature is present in the results for the four (4) subjects. Indeed, as the noise increases the relative EMG sensitivity also increases until it reaches a maximum, after which, it decreases even though the noise level continues to increase. It is noted however that for subject S8 (FIG. 9d), the last value of the noise (45 dB) is not reliable since the error margin (see vertical bar) is very large.

Figure 10:
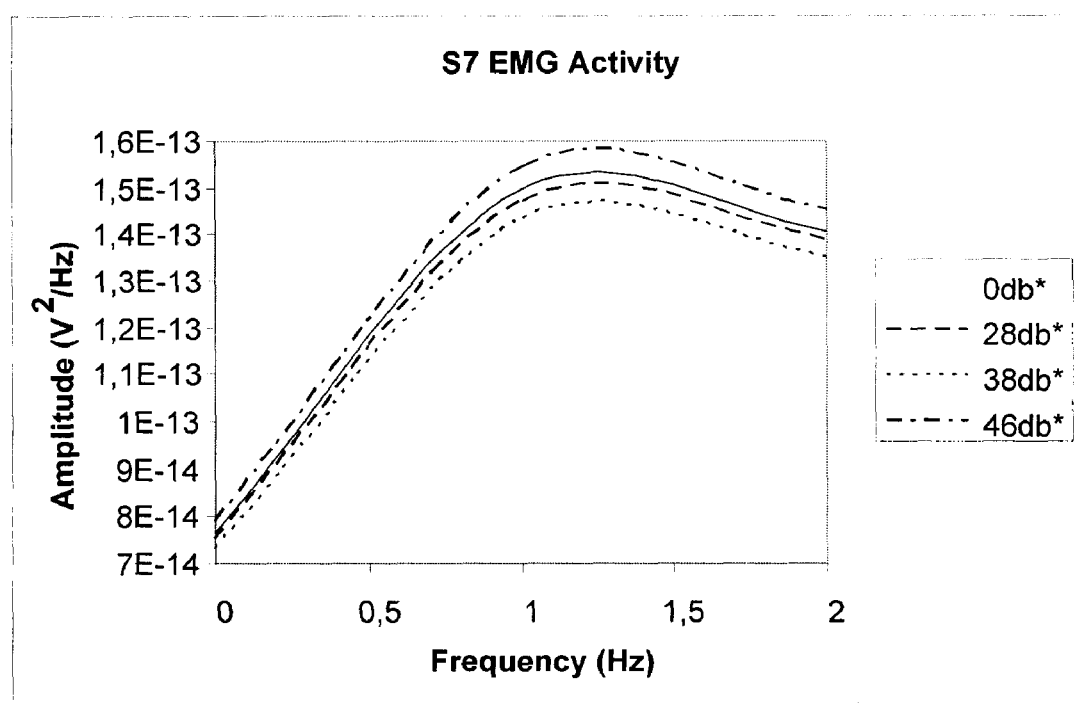
FIG. 10 is a graph illustrating the amplitude of the EMG power spectrum density as a function of frequency, for different levels of noise.

FIG. 10 shows the power spectrum density of the EMG activity of subject S7 at low frequencies, more specifically from 0 to 2 Hz with different auditory noise levels.

It is worth noting that, in all examples, the noise is a white noise generated by a noise generator and having a large spectrum wider than the auditory spectrum. However, because of mechanical and electrical resonances, the acoustic transducers inside the headphones change the spectrum of the white noise. Also, the headphones cannot reproduce the full spectrum of a white noise.

Therefore, the spectrum of the white noise is modified by the time that this noise reaches the cortex of the subject whereby the spectrum of the white noise reaching the subject's cortex is different from the original white noise spectrum. The subject's cortex therefore interprets a limited noise bandwidth between 5 to 10 KHz as a full white noise spectrum (Effective noise).

The third example allowed to show that stimulating one sense, for example the auditory sense, with a noise can influence and improve not only the sensitivity of another sense but also the postural balance and the general state of a person. Thus, via the SR phenomenon, the overall performance of the senses, the neural coordination, the visual perception and the postural balance of a subject can be improved.

Moreover, the SR phenomenon in human beings is shown to be a cross-modal and central process, not a local process localized in a certain sensory, reflex and/or motor mechanism of the subject as demonstrated in the past. Indeed, the results obtained with the third example imply that bio-signals of different nature resonate stochastically under the same conditions meaning that SR is happening in a common area of the human cortex.

Following the results obtained with the first, second and third examples, it can be seen that the system 10 can present two (2) modes of operation.

The first mode of operation of the system 10 consists of predetermining a noise level to be applied to the subjects. In this particular case, each subject is under the influence of the same level of noise. This case corresponds to the set-up in the second example where a same, predetermined level of auditory noise was applied to the different subjects. For example, the predetermined level of auditory noise can be programmed in the CPU 12 of the system 10.

In order to determine an appropriate predetermined level of auditory noise which can be used by a majority of subjects, a large number of tests can be performed in order to find the best value of noise level reflecting an average of the optimal levels of noise. This predetermined level of noise can further be refined and a predetermined noise level can be set for different groups of subjects themselves determined in relation to the age of the subjects, their gender, their physical condition, etc. Of course, a drawback of having a predetermined noise level is that this level does not always correspond to the optimal level of noise for each particular subject. Therefore, for a certain proportion of subjects, a predetermined level of noise may not improve the sensory, reflex and/or motor mechanisms of the subject, as an example for four (4) of fourteen (14) subjects as shown in FIG. 7.

The second mode of operation consists of a customized system 10 wherein each subject can adjust the level of noise according to his/her particular needs. Adjustment of the noise level may vary from one subject to the other, depending for example on their age, their physical condition, the nature of the stimulated sensory mechanism, their general health condition, etc. With the customized system 10, each subject determines his/her own optimal level of noise to be applied to the stimulated sensory mechanism for each particular situation.

FOURTH EXAMPLE

Figure 12:
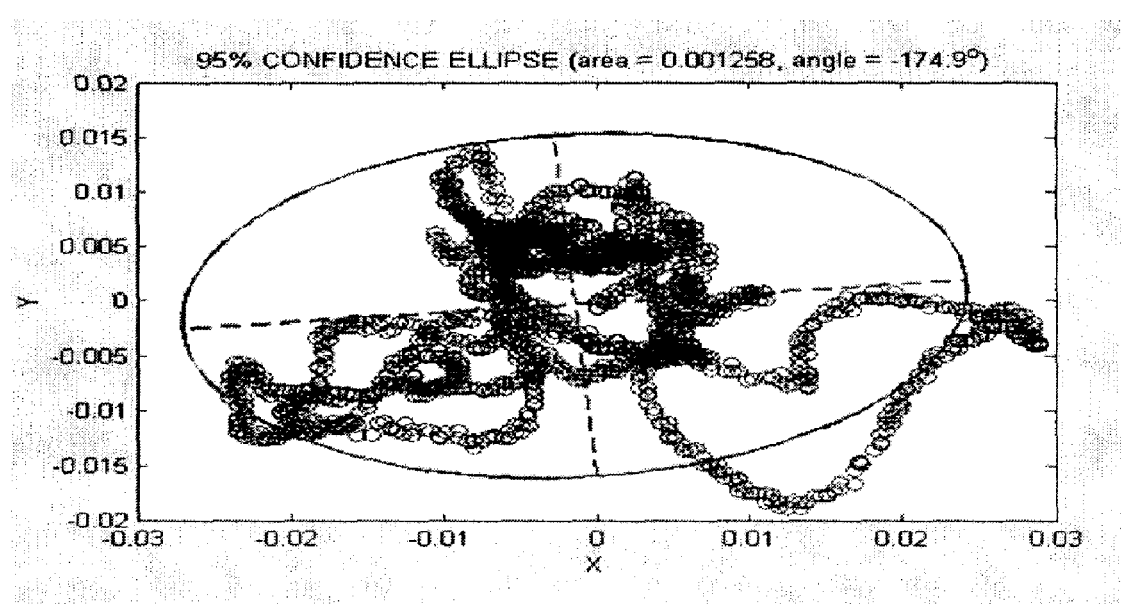
FIG. 12 is a graph showing the 95% confidence ellipse area from stabilograms.

This fourth example will be described with reference to FIGS. 11a, 11b and 11c showing graphs of the relative sweep area of three (3) subjects as a function of noise. The area was calculated from the 95% confidence ellipse area from stabilograms, which is shown in FIG. 12.

This fourth example is performed after the third example. In this fourth example, the relative sweep area was measured with the noise level for subjects S6, S7 and S8. As already indicated, the area is calculated from the 95% confidence ellipse area from stabilograms. A stabilogram measures the amplitude of movement in one, two or three directions. For instance, one dimension gives a length and two dimensions give an area. A magnetic position sensor 54 was attached to the left shoulder of the subjects as illustrated in FIG. 8. The stabilograms were measured in the x-y plane (see FIG. 8). Again the no noise condition is taken as the reference. In every trial, subjects were asked to stand with the feet straight and touching like in a tightrope position. Finally, three different noise levels were used.

FIFTH EXAMPLE

The fifth example is concerned with the investigation of the effects of an auditory noise, for example an auditory noise, on visual sensitivity of the subjects. For that purpose, seven (7) subjects were chosen in order to determine and measure the pattern of their respective visual threshold in the presence of auditory noise.

The age of the seven (7) subjects ranges from 22 to 38 years. The system 10 (see FIG. 3) is used to perform two simultaneous stimulations: (i) a visual stimulation provided by the visual stimulation device 24-6, and (ii) an acoustic stimulation provided by the acoustic stimulation device 24-5 formed by headphones.

The visual stimulation device 24-6 was controlled and monitored by the CU 12 and could produce 1024 gray levels that could all be presented simultaneously with a mean luminance of 43 cd/m2 and a refresh rate of 100 Hz. The visual stimulation device 24-6 was the only light source in the room. A sensor in the form of a photometer was integrated with the visual stimulation device 24-6 in order to calibrate its output. At a viewing distance of 2.20 m, the width and height of each pixel displayed by the visual stimulation device 24-6 were 1/64 deg of visual angle.

All the visual stimuli used in this experiment are the sum of two terms: a luminance modulation $L_{LM}(x,y)$ and a contrast modulation $L_{CM}(xy)$, given by:

$$L_{LM}(x,y)=L_0[M(x,y)+N(x,y)], \quad \text{Equation 1}$$

$$L_{CM}(x,y)=L_0[1+M(x,y)\cdot N(x,y)], \quad \text{Equation 2}$$

where $L_0$ represent represents the stimulus luminance average and the background luminance and $N(x,y)$ is an external carrier function.

The function $M(x,y)$ is defined as:

$$M(x,y)=1+S(x,y), \quad \text{Equation 3}$$

where $S(x,y)$ is the signal.

Figure 13:
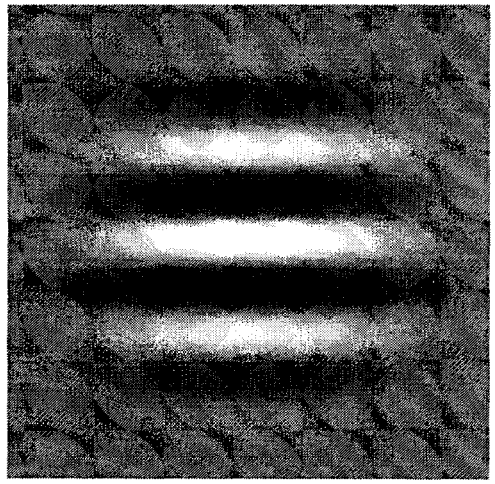
FIG. 13 is a visual representation of an example of a Gabor patch with a center spatial frequency $f$ of 1 cycle per degree of visual angle (cpd), a standard deviation of 1 deg, a randomized phase and a horizontal grating.

The signal function $(S(x, y))$ is a Gabor patch with a center spatial frequency $f$ of 1 cycle per degree of visual angle (cpd), a standard deviation $\rho$ of 1 deg, a phase p randomized at each stimulus presentation and a Michelson contrast C ($C_{LM}$ or $C_{CM}$ depending on the type of modulation) that varied according to the task, $S(x, y)$ is given by:

$$S(x, y) = C\sin(fr_1 + p)\exp\left(-\frac{x^2 + y^2}{2\sigma^2}\right), \quad \text{Equation 4}$$

where $r_1$ can be the direction x or y. FIG. 13 shows and example of the signal function $S(x, y)$ with an horizontal grating.

Figure 14:
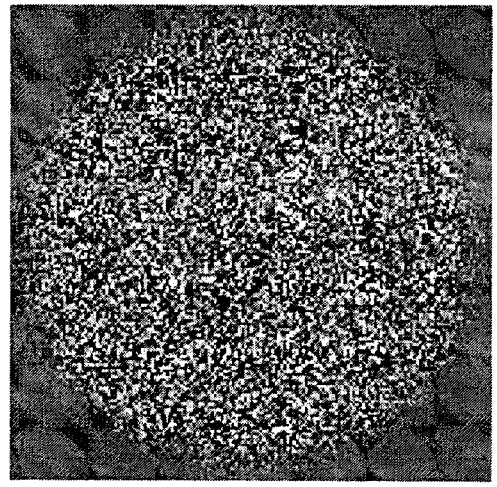
FIG. 14 is a visual representation of an example of a Gaussian distribution centered on 0.

The carrier function $(N(x,y))$ generated a matrix of 320 times 320 pixels (5 times 5 deg), each element being randomly selected from a Gaussian distribution centered on 0, as shown in FIG. 14.

Figure 15:
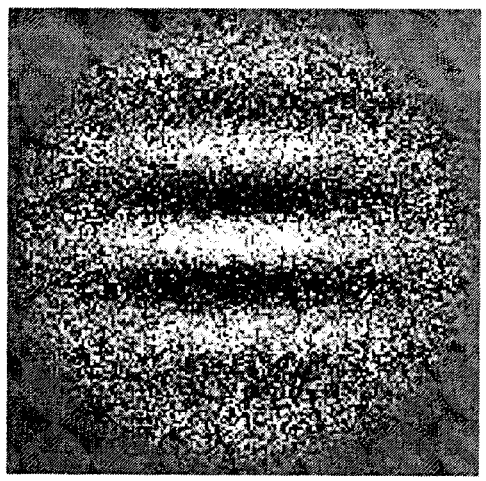
FIG. 15 is a visual representation of an example of a horizontal luminance-modulated stimuli (LM) grating with Gaussian noise.
Figure 16:
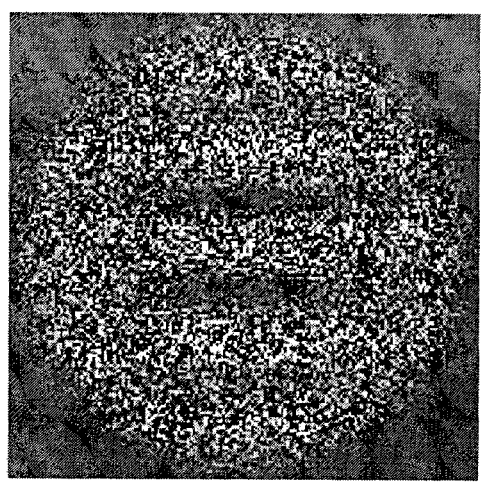
FIG. 16 is a visual representation of an example of a horizontal contrast-modulated stimuli (CM) grating with Gaussian noise.

A 2-alternative-forced-choice method was used: every presentation contained a carrier modulated by a signal but the Gabor patch was either horizontal or vertical. The task was to discriminate between vertical or horizontal luminance-modulated stimuli (LM), as characterized by Equation 1, and contrast-modulated stimuli (CM), as characterized by Equation 2. FIGS. 15 and 16 show examples of a horizontal LM grating and CM grating, respectively, with Gaussian noise.

For a given task, e.g. detection of a LM or CM signal, the signal and carrier modulation types were fixed and known to the subject. The stimuli were presented for 500 ms with stimuli intervals of the same duration. The spatial window was circular with a full contrast plateau of 4 deg width and soft edges following a Gaussian distribution with a standard deviation of 0.25 deg.

In a first step, the seven (7) subjects (not shown) were seated at a distance of 2.20 m from the visual stimulation device 24-6 and were asked whether the displayed grating was horizontal or vertical for each of the LM and CM stimuli. After each trial, a feedback sound indicated to the subject if his or her response was correct. To evaluate the LM and CM thresholds, a 2-down-1-up procedure was used, that is, after two consecutive correct responses the dependant variable, which varied depending on the task, was decreased (or increased when the dependant variable was a noise contrast) by 10% and increased (or decreased) by the same proportion after each incorrect response resulting in a threshold criterion of 70.7%. The threshold was defined as the geometric mean of the last six (6) inversions (peaks) of the dependent variable values. This first step, without any auditory noise was used as a control.

In a second step, the seven (7) subjects were subjected to an auditory noise through the headphones 24-5. The subject was then asked again whether the displayed grating was horizontal or vertical for each of the LM and CM stimuli while listening to the auditory noise produced through the headphones 24-5 (with a cut-off of 15 kHz). The LM and CM thresholds were then measured for five (5) auditory levels, using the same 2-down-1-up procedure as described in the first step.

Thus, six (6) auditory conditions (control plus five noise levels) were measured and five (5) thresholds (5 separate staircases) were established for each condition and averaged.

Results for the LM stimuli are shown in FIGS. 17a, 17b and 17c while the results for the CM stimuli are shown in FIGS. 18a, 18b and 18c. In these experiments we have used calibrated instruments in a SPL (Sound Pressure Level) normalized scale, wherein 0 dBSPL equals 20 µP (micro Pascal) Again, FIGS. 17a-17c and 18a-18c generally show and still demonstrate the typical SR signature; as the noise increases the visual threshold also decreases (which is equivalent to better sensitivity) until it reaches a minimum, after which, it increases even though the noise level continues to increase. In these graphs, better sensitivity means lower values because data are presented as thresholds. These data demonstrate that contrast sensitivity, a fundamental function of visual processing, is improved by the same mechanisms as demonstrated for the other senses. The data also demonstrate that this is true for different levels of form perception i.e. first and second-order visual processing.

The Melnikov Theory

The classical theory of Melnikov is used to understand and analyze systems that show transitions. Since the human cortex induces transitions (improvements) of one sense by using the energy of a signal applied to another sense, the theory of Melnikov can be used to explain the cross-modal interactions occurring in the human cortex.

More specifically, the theory of Melnikov shows that the SR phenomenon is chaotic and explains the role of the frequency spectrum of the noise in the improvement of the signal-to-noise ratio (SNR). This theory can further be extended to the improvement of the SNR through the addition, not only of noise, but also of harmonic or deterministic excitations.

First, the theory of Melnikov assumes that the transitions are always chaotic.

Then, the necessary condition for inducing chaos in a system is given by:

$$F_d + \sum_{k=1}^{K} A_k S_k(\omega_k) + F_N > 0, \quad \text{Equation 5}$$

where $F_d$ is related to dissipated energy and the two other terms are related to excitation energy. The excitation energy can be deterministic (second term) or stochastic (third term). The deterministic excitations usually are harmonic signals at different frequencies and the stochastic excitations are white noise.

The Melnikov Necessary Condition (MNC) for occurrences of transitions, in presence of a visual or auditory signal, when the tactile sense is tested, is given by:

$$F_d + \sum_{k=1}^{K} A_k^T S(\omega_k) + \sum_{l=1}^{L} A_l^{V,A} S(\omega_l) + F_N^T > 0, \quad \text{Equation 6}$$

where the first summation represents the deterministic harmonic in the tactile signal and the second summation is the harmonic excitation in the visual or auditory signal. The best frequencies for generating transitions are the ones contained in a band near the maximum of the MSF (Melnikov Scale Factor). The MSF is a frequency function which gives the frequency components that are most effective in inducing transitions. The amplitude of these frequencies improves the performance of the tactile mechanism.

Therefore, the theory of Melnikov shows that a deterministic signal, instead of a white noise, can also act upon the multi-sensory integration mechanism for creating an improved state of functionality. This phenomenon is a deterministic synchronization-like phenomenon.

Although the present invention has been described in the foregoing specification by means of a non-restrictive illustrative embodiment, this illustrative embodiment can be modified at will, within the scope of the appended claims, without departing from the scope, spirit and nature of the subject invention.

What is claimed is:

1. A method for improving sensitivity of a first sensory, reflex and/or motor mechanism of a subject, comprising stimulating, using a sensory, reflex and/or motor mechanism stimulation device, a second sensory, reflex and/or motor mechanism of the subject, wherein:
   stimulating a second sensory, reflex and/or motor mechanism of the subject comprises applying, using the stimulation device supplied with a source of stimulation signal, a noise to the second sensory, reflex and/or motor mechanism; and
   applying a noise to the second sensory, reflex and/or motor mechanism improves the sensitivity of the first sensory, reflex and/or motor mechanism due to cross-modal SR interactions,
   wherein the applying step comprises an operation selected from the group comprising:
      applying, using an acoustic stimulation device, an auditory noise to at least one ear of the subject,
      applying, using a visual stimulation device, a visual noise to at least one eye of the subject,
      applying, using a tactile stimulation device, a tactile noise to at least one part of the subject's body, and
      applying, using a thermal stimulation device, a thermal noise to at least one area of the subject's body.

2. A method as defined in claim 1, wherein the noise is an effective noise.

3. A method as defined in claim 1, wherein stimulating a second sensory, reflex and/or motor mechanism of the subject comprises applying, using the stimulation device, a direct stimulation to a particular area of the subject's body.

4. A method as defined in claim 1, wherein applying a noise to the second sensory, reflex and/or motor mechanism comprises applying a predetermined noise level.

5. A method as defined in claim 1, wherein applying a noise to the second sensory, reflex and/or motor mechanism comprises adjusting the noise to a level customized to the needs of the subject.

6. A method for improving sensitivity of a first sensory, reflex and/or motor mechanism of a subject, comprising:
   stimulating, using a sensory, reflex and/or motor mechanism stimulation device, a second sensory, reflex and/or motor mechanism of the subject; and
   applying a noise to the second sensory, reflex and/or motor mechanism improves the sensitivity of the first sensory, reflex and/or motor mechanism due to cross-modal SR interactions,
   wherein the stimulating step comprises:
      applying, using the stimulation device supplied with a source of stimulation signal, a noise to the second sensory, reflex and/or motor mechanism,
      applying, using a plurality of stimulation devices, a type of stimulation selected from a group comprising:
         (i) a differential stimulation by stimulating two different areas of the subject's body in order to stimulate a first region of the subject's body between said two different areas,
         (ii) a distributed stimulation by stimulating several areas of the subject's body in order to stimulate a second region of the subject's body covered by said several areas, and
         (iii) a plurality of different stimuli.

7. A system for improving sensitivity of a first sensory, reflex and/or motor mechanism of a subject, comprising:
   a plurality of stimulation signal sources; and
   a plurality of stimulators, each stimulator being responsive to a corresponding stimulation signal from a corresponding source and producing, in response to the corresponding stimulation signal, a noise applied to a second sensory, reflex and/or motor mechanism of the subject;
   wherein application of the noise to the second sensory, reflex and/or motor mechanism improves the sensitivity of the first sensory, reflex and/or motor mechanism of a subject due to cross-modal SR interactions, and
   wherein the plurality of stimulators is configured to apply a type of stimulation selected from a group comprising:
      a differential stimulation by stimulating two different areas of the subject's body in order to stimulate a first region of the subject's body between said two different areas,
      a distributed stimulation by stimulating several areas of the subject's body in order to stimulate a second region of the subject's body covered by said several areas, and
      a plurality of different stimuli to the patient's body.

8. A system as defined in claim 7, wherein at least one source comprises a conditioner of the corresponding stimulation signal, the corresponding stimulation signal being conditioned prior to being supplied to a corresponding stimulator.

9. A system as defined in claim 7, wherein at least one stimulator includes a sensor for measuring the noise applied to the second sensory, reflex and/or motor mechanism of the subject.

10. A system as defined in claim 7, wherein each stimulator is selected from a group consisting of a visual stimulation device, a vibratory stimulation device, an electromagnetic stimulation device, a thermal stimulation device, a tactile stimulation device and an acoustic stimulation device.

11. A system as defined in claim 7, wherein at least one stimulator applies a direct stimulation to a particular area of the subject's body.

12. A system as defined in claim 7, wherein at least one source and at least one corresponding stimulator are so configured as to apply a predetermined noise level to the second sensory, reflex and/or motor mechanism.

13. A system as defined in claim 7, wherein at least one source is so configured as to adjust the noise applied to the second sensory, reflex and/or motor mechanism to a level customized to the needs of the subject.

14. A system as defined in claim 7, further comprising an interface for connecting the system to a computer for transferring thereto information about a stimulation process.

* * * * *